United States Patent [19]

Gnecco

[11] 4,040,844
[45] Aug. 9, 1977

[54] PORCELAIN TOOTH AND METHOD OF MANUFACTURE

[76] Inventor: Rafael Gnecco, 3820 Waldo Ave., Bronx, N.Y. 10463

[21] Appl. No.: 585,529

[22] Filed: June 10, 1975

[51] Int. Cl.² .......................... A61C 13/08; C09K 3/00
[52] U.S. Cl. ........................................ 106/35; 106/45; 32/8; 32/15
[58] Field of Search .................... 106/35, 45; 260/37; 32/8, 15

[56] References Cited

U.S. PATENT DOCUMENTS

| | | | |
|---|---|---|---|
| 2,443,318 | 6/1948 | Lee et al. | 106/45 |
| 2,652,338 | 9/1953 | Greger | 106/45 |
| 3,400,097 | 9/1968 | Weinstein | 260/37 R |
| 3,621,576 | 11/1971 | Gnecco | 32/8 |
| 3,766,650 | 10/1973 | Gnecco | 32/8 |
| 3,880,662 | 4/1975 | Daskalon | 106/35 |

OTHER PUBLICATIONS

Restorative Dental Materials, Peyton et al., p. 528, 1971.

*Primary Examiner*—Theodore Morris

*Attorney, Agent, or Firm*—James E. Bryan

[57] ABSTRACT

A porcelain tooth structure and method of making the same in which a powder-form porcelain is mixed with an adhesive, in an amount suffficient to form a coherent mass of the porcelain, to form a workable paste, the paste is formed into a tooth structure having the general shape of a desired, finished tooth, preferably by molding in a metal, plastic or rubber mold, the molded tooth is dried, generally at a temperature between ambient temperature and about 600° F and the adhesive in at least a part of the tooth structure is rendered water-resistant by utilizing an inherently water-resistant adhesive or treating a water-soluble adhesive with an agent which renders the adhesive water-resistant, such as a solvent, a hardening agent for the adhesive, a water-immiscible oil or another agent which combines with the adhesive by chemical reaction, physico-chemical reaction or physical action, either during the mixing of the porcelain and adhesive or after the drying of the tooth structure. The tooth structure may thereafter be semi-baked at a temperature sufficient to form a concretious tooth structure, generally above about 1200° F, but below the vitrification temperature of the procelain.

5 Claims, No Drawings

PORCELAIN TOOTH AND METHOD OF MANUFACTURE

BACKGROUND OF THE INVENTION

The present invention relates to unbaked, porcelain teeth and methods of making the same. More specifically, the present invention relates to water-resistant, unbaked, porcelain teeth and methods of making the same.

In the art of manufacturing prosthetic dental appliances, there are several procedures for manufacturing porcelain teeth therefor. However, certain basic steps are followed in all such procedures. These include forming a porcelain paste of porcelain and an agglutinant or binder, molding to the approximate shape of the desired tooth, drying to remove moisture and harden the agglutinant or binder, heating to an elevated temperature to vitrify the porcelain, soaking at this temperature to glaze the outside surfaces and shaping and fitting the tooth to the patient's exact needs and fitting it to the appliance by grinding or adding porcelain as needed, usually in a dental laboratory under the direction and instruction of the dentist.

In accordance with one standard procedure, fully vitrified porcelain teeth are sold in the completely finished state. A tooth is then selected that approximately meets the requirements in a particular case and is then fitted exactly to the patient's requirements and to the appliance by grinding and/or adding porcelain of a lower fusion point than that of the porcelain utilized in the manufacture of the tooth. The modified tooth is then fired to make it a somewhat integral structure with the added porcelain. However, in working with such completely vitrified porcelain teeth, numerous difficulties are encountered. First, such completely vitrified teeth are hard and brittle and are, therefore, difficult to grind. In addition, such grinding violates the integrity of the surface of the tooth. Finally, only porcelain of a lower fusion point than that of the tooth proper can be added to build-up the tooth where necessary. Since the fully vitrified tooth is hard and nonporous, the added porcelain cannot diffuse into the tooth proper, thus resulting in a final structure which cannot be considered a monolithic or homogeneous structure, and has a poor bond or juncture between the tooth proper and the added porcelain, even after firing to full vitrification. It is also obvious that the added porcelain will have a somewhat lower structural strength than the tooth proper.

In order to overcome the disadvantages of shaping and fitting the hard, brittle, fully vitrified tooth and make possible the addition of porcelain of the same fusion point, it is also common practice to make porcelain teeth in the unbaked or "green" state, and, thereafter, fire the tooth to the fusion or vitrification point. More specifically, a porcelain paste is formed of porcelain and an agglutinant or binder, the paste is shaped or molded to the desired shape and contour and the shaped tooth is then dried at a low temperature, about 600° F, to remove moisture and harden the agglutinant or binder. In this state, the tooth is oversized (about twice the size of the finished tooth), is easily damaged and is difficult to handle and shape and fit. These drawbacks are attributable to the nature of the agglutinants presently utilized in the formation of the green tooth. All presently used agglutinants, such as starch, lose their adhesive properties when exposed to water either due to the fact that they are water-soluble or are destroyed during the drying step. As a result, the green tooth tends to disintegrate when moistened. This makes it impossible to adapt the tooth, since moist porcelain must usually be added. It has also been found that the green tooth is generally held together by an adhesive film on the surface and the interior is powdery and incohesive. Thus, upon grinding, the powdery or unconsolidated interior is exposed. This characteristic structure is believed to be caused by the fact that many presently used agglutinants are expelled from the porcelain during the process of drying the shaped structure. Finally, agglutinants presently used are usually of vegetable origin (generally a starch) and such agglutinants burn when the tooth is fired to the fusion or vitrification temperature. As a result, a small amount of residue or ash is produced which causes some discoloration of the finished, vitrified tooth.

Yet another commercial technique is set forth in applicant's U.S. Pat. Nos. 3,621,576 and 3,766,650, the teachings of which are incorporated herein by reference. In accordance with this technique, teeth are supplied to the customer in a semi-baked state and the customer is instructed to adapt the tooth and thereafter fire the same to the vitrification temperature. This technique overcomes the disadvantages of working with hard, brittle fully-vitrified teeth and permits the addition of porcelain having the same fusion point as the tooth proper during adaptation. In summary, a tooth is prepared, in accordance with the above-mentioned patents, by making a green tooth or biscuit in the usual manner and then baking the biscuit at a temperature which converts it to a hard, concretious or consolidated state (above about 1200° F) but below the vitrification or fusion point of the porcelain utilized (usually about 50° F below the fusion point). In this state, the tooth is water-insoluble, is essentially resistant to damage, during handling and adapting, has a rough, porous surface, which accepts porcelain of the same fusion point as the tooth proper, after firing to vitrification, forms a monolithic or homogeneous structure of the tooth proper and the added porcelain and is substantially the same size as the fully vitrified or finished tooth. The customer then adapts the tooth, as indicated above, and fires it to the vitrification point of about 1600° F or 2300° F or higher, depending upon whether the porcelain utilized has a low or high temperature fusion point. While this technique overcomes numerous of the disadvantages of working with green, unbaked teeth, at the customer level, particularly the problem of water-solubility, certain problems are still associated with the handling of and working with the biscuit during the manufacture of such semi-baked teeth. For example, the green tooth must be adapted to some degree, by trimming and sometimes adding porcelain prior to the semi-baking step, and the handling and working of the tooth at this stage is facilitated by practicing the present invention in the preparation of the green tooth prior to the semi-baking step.

It is, therefore, an object of the present invention to provide an improved porcelain tooth and a method of manufacture which overcomes the previously-mentioned disadvantages of the prior art.

Another object of the present invention is to provide an improved green, porcelain tooth and method of manufacture.

Yet another object of the present invention is to provide an improved semi-baked porcelain tooth and method of manufacture.

A further object of the present invention is to provide a water-resistant, green, porcelain tooth and method of manufacture.

Another and further object of the present invention is to provide an improved green, porcelain tooth, and method of manufacture, which can be molded in any molding apparatus, such as a solid plaster or metal mold, a semi-solid wax or plastic mold, an elastic or rubber mold, etc.

A still further object of the present invention is to provide an improved green, porcelain tooth, and method of manufacture, which is rugged and easy to handle.

Another object of the present invention is to provide an improved green, porcelain tooth, and method of manufacture, which can be cut, shaped, handled and adapted without affecting its structure, as its basic form, color, strength, etc.

A further object of the present invention is to provide an improved green, porcelain tooth, and method of manufacture, which can be adapted, as by trimming, grinding, adding porcelain, etc. witout affecting its structure.

Yet another object of the present invention is to provide an improved green, porcelain tooth, and method of manufacture, which can be converted to an improved finished or completely vitrified tooth, as a finished tooth of reduced, desired size and shape, etc.

Another object of the present invention is to provide an improved green porcelain tooth and method of manufacture, which is of uniform or homogeneous structure throughout, as consistency and cohesiveness, as opposed to a non-homogeneous or non-uniform structure, as a powdery interior, a non-uniform and/or different structure between the tooth proper and porcelain added during adaptation, a weak or improper bond between the tooth proper and porcelain added during adaptation, etc.

A further object of the present invention is to provide an improved green, porcelain tooth and method of manufacture which results in reduced waste.

Another and further object of the present invention is to provide an improved green, porcelain tooth, and method of manufacture, which can be moistened and/or have moist porcelain added thereto without altering its basic shape or size, as by warping, wholly or partially disintegrating, etc.

Another object of the present invention is to provide an improved green, porcelain tooth and method of manufacture wherein a water-resistant or water-insoluble agglutinant or binder is utilized.

Yet another object of the present invention is to provide an improved green, porcelain tooth and method of manufacture wherein a water-soluble agglutinant or binder is utilized and said water-soluble agglutinant or binder is rendered water-resistant, either prior to shaping or molding or after shaping and molding.

A further object of the present invention is to provide an improved green, porcelain tooth and method of manufacture wherein a water-soluble agglutinant or binder is utilized and said agglutinant is rendered water-resistant by treating said agglutinant with a chemical which renders the said agglutinant or binder water-resistant, as by chemical reaction therewith, physico-chemical reaction therewith, mild heating during drying, exposure to light, physical combination therewith, etc., either before shaping or molding, after shaping or molding or during the drying of the shaped or molded structure.

A still further object of the present invention is to provide an improved green, porcelain tooth and method of manufacture wherein an agglutinant or binder is utilized which leaves no residue and thus does not affect the structure thereof, as the color, etc., when subsequently baked to the concretion point or the vitrification point.

Another and future object of the present invention is to provide an improved green, porcelain tooth and method of manufacture wherein an agglutinant or binder is utilized which is not expelled or destroyed, as by volatilization, etc., during drying, but is expelled by volatilization during baking to the concretion point or the vitrification point.

These and other objects and advantages of the present invention, as well as others obvious to one skilled in the art, will be apparent from the following description.

SUMMARY OF THE INVENTION

The present invention relates to a green, porcelain tooth structure, comprising porcelain in admixture with an adhesive material, in an amount sufficient to form a cohesive mass of said porcelain, and formed into a dry, coherent mass having the general shape of a desired finished tooth, at least a part of said structure being water-resistant, and a method of making the same wherein at least a part of the adhesive portion of said coherent mass is rendered water-resistant, during formation of said admixture or after the formation of said coherent mass. The dry coherent mass may be further treated by heating to the concretion point of said mass but below the fusion point of the porcelain.

DESCRIPTION OF THE PREFERRED EMBODIMENTS

In accordance with one embodiment of the present invention, a porcelain material is first mixed with a water-resistant binder.

The procelain utilized may be any of the standard porcelain materials supplied for purposes of tooth manufacture. Usually, the grade or type utilized is classified according to its fusion or vitrification point. For example, a so-called "low" fusion point porcelain has a fusion point of about 1500° F, a so-called "intermediate" fusion point porcelain has a fusion point of about 1900° F and a so-called "high" fusion point porcelain has a fusion point of about 2300° F or higher. Porcelains with other fusion points can of course be obtained and utilized. While the entire tooth structure is made of a single porcelain, it is normal practice to employ two and sometimes more than two porcelains of different colors, depending upon the portion of the tooth formed.

The adhesives may be any commercially available adhesive, which is at least water-resistant and preferably water-insoluble. The adhesive should also be one that will not be expelled at drying temperatures, below about 600° F, but will be expelled at higher "baking" temperatures, between the drying temperature and the concretion temperature and/or vitrification temperature. Since adhesives which are expelled by burning leave a small amount of ash which has a slight discoloring effect, it is also preferred that the adhesive be one which is expelled by volatilization above the drying temperature.

The relative amounts of adhesive and porcelain in the mixture are determined by the technician and are known to those skilled in the art. Specifically, the amount of adhesive is an amount just sufficient to form a workable paste. Since the tooth structure is formed by hand by the technician or is loaded into a mold by hand, the admixture should have a putty-like consistency and should not stick to the fingers, forming tools, such as a spatula, or the mold utilized.

After the paste admixture is formed, the paste is formed into a coherent mass, generally of the shape of the desired finished tooth. Usually, an appropriate mold is utilized. When utilizing the admixtures of the present invention, any type of mold may be employed, such as a solid (metal or plaster) mold, a semi-solid (plastic or wax) mold or an elastic (rubber) mold. Preferably, a two-part mold is utilized, one for the lingual portion and one for the labial portion, but molds in three or more parts can be used. After packing with the appropriate porcelain paste, the parts of the mold are put together and clamped tightly.

The cohesive mass is then dried in the mold or after removal. The drying temperature is dependent upon the adhesive utilized and again is within the purview of one skilled in the art. More specifically, the drying temperature may be anywhere from ambient temperature to about 600° F.

The drying time also varies, depending upon the adhesive used and/or the temperature. Drying times from 10 minutes to one hour are typical.

The dried, cohesive mass is then removed from the mold and worked as necessary. Such working may include minor adjustments by shaping or removing material with a tool, such as a spatula, or building-up a portion by adding porcelain paste. Usually, only minor shaping is required, since the mold is accurately formed and all that needs to be done is to remove protrusions built-up at the mold juncture.

The green tooth in this form is now ready for customer adaptation, finishing and mounting. As previously indicated, this green tooth is water-resistant and, therefore, can be moistened and/or modified by adding moist porcelain, having the same fusion point, to build-up portions thereof, as necessary, to adapt it to the patient's needs and/or the prosthetic appliance. Due to the water-resistance of the green tooth structure, such moistening and/or addition of moist porcelain can be carried out without disintegration, warping or otherwise affecting the basic shape of the tooth, unlike presently known green teeth. The water-resistance should be such that the green tooth can be completely submerged in water for several minutes without even the slightest effect on its shape. Being water-resistant, the adhesive is not expelled during drying and, hence, the interior of the green tooth is solid, cohesive and water-resistant, rather than powdery as are presently produced green teeth. The green tooth structure, as manufactured in accordance with the present invention, also has the same properties of consistency and cohesiveness throughout and is rugged, easy to handle, easy to grind and easy to build-up by the addition of moist porcelain.

The tooth is supplied to the customer in this form and the customer is instructed to adapt the tooth in the usual manner and thereafter fire it to the fusion or vitrification temperature.

Upon baking or firing to the fusion point, the size of the green tooth is reduced to the size desired, usually about half size. A green tooth, in accordance with the present invention, when fired to the vitrification temperature and reduced in size, maintains its desired shape and is the exact shape required in the reduced-size form. Also, during the baking or firing, the adhesive is substantially completely expelled by volatilization, thus leaving no discoloring ash as a residue.

While only those portions of the tooth which require adaptation and/or will be subjected to contact with moisture and/or moist porcelain can be formed with the water-resistant adhesive and the remainder with a water-soluble adhesive, it is preferred that the water-resistant adhesive be used throughout, since the tooth is relatively porous and moisture can be absorbed into the interior rather readily.

As previously indicated, the green tooth as thus prepared can be further treated by the manufacturer to produce a semi-baked tooth, as taught by U.S. Pat. Nos. 3,621,576 and 3,766.650. Specifically, the green tooth structure is baked to the point of concretion but below the vitrification temperature. Usually, this temperature is above about 1200° F and about 50° below the vitrification temperature. While the adhesive will generally be volatilized and expelled during this treatment, the adhesive is no longer necessary, since the semi-baked tooth is mechanically strong, non-brittle, completely coherent, and easily adapted by trimming, grinding and the addition of moist porcelain of the same fusion point as the porcelain of the portion of the tooth to be built up. It is also sufficiently porous that the added porcelain will be "absorbed" to some extent and an excellent bond between the tooth proper and the added porcelain and a monolithic or homogeneous structure is formed, upon firing to the vitrification temperature. In this technique, all or only those parts of the green tooth which usually require adaptation can be semi-baked and the remainder completely vitrified. The customer is instructed to adapt and fire the tooth to the vitrification point in the usual manner.

The tooth structures can be manufactured in various forms, such as complete teeth, hollow shells or thimbles, porcelain jackets, partial teeth, either solid or hollow, faces, one-half or one-third crowns or in any form necessary for the manufacture of prosthetic dental appliances or as required by the dental profession.

In accordance with another embodiment of the present invention, a water-soluble adhesive, such as celluloses and other vegetable- and animal-type adhesives, may be utilized and a chemical added thereto to make it water-resistant prior to admixture with the porcelain. One such technique involves dispersing the adhesive in a solvent, such as a conventional laquer thinner. The solvent should not volatilize at the drying temperature but should volatilize at a temperature above the drying temperature, thus volatilizing the adhesive along with it during baking. A water-soluble adhesive may also be treated with a preservative or hardening agent, such as formaldehyde, which will render the adhesive water-resistant when exposed to light. In a similar technique, a water-soluble adhesive can be treated with an inorganic nitrate, such as silver nitrate, which renders it water-resistant when exposed to light.

In a variant of the previously-described technique, of treating the adhesive with a chemical to render a water-soluble adhesive water-resistant, the green tooth is formed from an admixture of porcelain and a water-soluble adhesive, molded, dried and thereafter treated with the chemical agent to render the adhesive water-resistant. In this technique, the previously mentioned treating agents may all be utilized and, after moistening or otherwise contacting the tooth with the treating agent, it is dried again, usually at ambient or very low temperatures. Since, the green tooth is porous, the treating agent will be absorbed to essentially the same extent that moisture would be absorbed and, hence, the tooth will be sufficiently water-resistant to be unaffected by contact with moisture and/or the addition of moist porcelain.

The following specific examples are illustrative of the present invention.

EXAMPLE 1

In the following example, a water-soluble adhesive is converted to a water-resistant binder prior to molding of the green tooth structure.

The adhesive was first prepared by adding 1 oz., by weight, of distilled water to 1 oz., by weight, of cellulose powder and mixed until the cellulose swelled. An additional 7 ozs., by weight, of distilled water was added with mixing. At this point, the adhesive is a water-soluble adhesive. 2 grams of formaldehyde was then added with mixing to render the adhesive water-resistant.

2 drops of McCormick green food coloring (manufactured by McCormick & Co., Baltimore, Maryland) were added to the adhesive to color-code the same.

1 oz., by volume, of distilled water was thoroughly mixed with 1 oz., by volume, of "Stern V-65" porcelain (manufactured by Stern Dental, Mount Vernon, N.Y.). The mixture was allowed to settle for 10 minutes and the water was decanted. Excess moisture was removed by contacting the porcelain with an adsorbent paper tissue until the porcelain was damp but flaky in character.

1 oz., by volume, of the porcelain, as prepared, was thoroughly mixed with a sufficient amount of the prepared, green-coded adhesive to produce a mixture of putty-like consistency which would not stick to the fingers, tools or molds (about 30 drops). A green-coded paste of adhesive and porcelain was thus produced.

A second portion of adhesive was prepared and color-coded with McCormick yellow food coloring, in the same manner as above. A damp, flaky mass of "Stern V-62" porcelain (manufactured by Stern Dental) was prepared and mixed with the yellow-coded adhesive, in the same manner as above, to produce a yellow-coded porcelain paste.

One part of a metal mold for the incisal portion and labial face of a tooth structure was loaded with the green-coded, porcelain paste by pressing the same into the mold with the fingers and/or a spatula.

A second part of the mold for the gingival portion and lingual face of the tooth was similarly loaded with the yellow-coded, porcelain paste.

The mold halves were then placed together and tightly clamped.

The tooth structure, while still in the mold, was dried for 10 minutes at 200° F.

When drying was completed, the tooth structure was removed from the mold and trimmed, as necessary, with a spatula.

The unbaked or green tooth structure is now ready for sale to the customer.

The customer is instructed to adapt the tooth, in the conventional manner, and thereafter vitrify the same by firing it in an oven, under 30 lbs. of vacuum, to a temperature of 1600° F and, when the temperature has reached 1800° F, removing it from the oven and cooling it under a glass cover.

EXAMPLE 2

A water-resistant, green tooth structure was produced, in the following example, by treating the tooth with a chemical after molding and drying.

1 oz., by volume, of wheat starch (liquid laundry starch) was color-coded with 2 drops of green food coloring, in the same manner as in Example 1.

A mass of damp, flaky Stern V-65 porcelain was prepared, as in Example 1.

The green-coded adhesive was then mixed with the prepared porcelain to produce a green-coded porcelain paste, in the same manner and using the same proportions as in Example 1. Slightly more mixing was, however, required in this case. Thus, a green-coded porcelain paste for the incisal portion of the tooth was produced.

A yellow-coded, porcelain paste for the gingival portion of the tooth was prepared in the same manner, as above and as in Example 1.

The prepared porcelain pastes were then molded, as in Example 1, and dried for 10 minutes at 300° F.

The molded green tooth structure was then moistened with diluted formaldehyde (2 to 3 drops), being careful not to disturb the tooth. Complete moistening is necessary.

The treated tooth was dried under a 100 watt light bulb (about 8 inches away) for 15 minutes.

A water-resistant, green, porcelain tooth structure, ready for the customer, was thus produced and the customer is instructed to finish the tooth, in the manner set forth in Example 1.

EXAMPLE 3

An unbaked or green, water-resistant tooth structure was prepared, in the following example, by treating the tooth with a chemical agent after molding and drying.

A green-coded porcelain paste was prepared for the labial portion of the tooth, in the same manner and utilizing the same proportions as in Example 1, except that casein glue (Elmer's white glue manufactured by the Borden Co.) was used as an adhesive.

A yellow-coded porcelain paste was prepared for the lingual portion of the tooth, in the same manner and utilizing the same proportions as in Example 1 except, again, the casein glue was used as an adhesive.

A metal mold was lubricated with a light coating of petroleum jelly and the tooth was molded, as in Example 1. Drying was conducted at 200° F for 10 minutes.

The green tooth structure was then carefully submerged in olive oil and allowed to drip dry for 1 hour.

A water-resistant tooth ready for customer use was produced.

In this case, the customer is instructed to fire to a temperature of about 1500° F. The customer is also advised that the tooth will initially turn dark and smoke but, when the temperature reaches about 2000° F, the smoking will cease and the black color will disappear.

EXAMPLE 4

A water-resistant adhesive was prepared by mixing 2 grams, by volume, of cellulose binder with one-half oz., by volume, of acetone.

1 oz., by weight, of dry, flaky porcelain, prepared as in Example 1, was mixed with one-fourth oz., by volume, of the prepared adhesive. Mixing must be fast, in this case, since the adhesive dries quickly, but a paste of the same consistency is produced.

A porcelain paste, utilizing the prepared adhesive, was then prepared for the labial portion of the tooth in the same manner as above.

The tooth was then molded as in Example 1. Drying was accomplished in a well-ventilated environment at ambient temperature.

The water-resistant, green or unbaked tooth is supplied to the customer with the usual instructions for finishing. In this case, the tooth darkens during firing but the color disappears at about 1000° F.

A large number of adhesives which are water-resistant or water-insoluble or which are water-soluble and can be made water-insoluble or water-resistant are suitable for use as binders in the present invention.

Suitable water-insoluble adhesives include the natural resins, such as copal, dammar, sandrac gum, Manila gum copal, colophony, etc., as well as a number of synthetic resins. Casein is almost water-insoluble and may be used in its untreated state or treated to increase its insolubility. Certain of the alginates are also water-insoluble.

Solvents such as ether, alcohol, chloroform, etc. may be used as a vehicle for these water-insoluble materials.

Water-soluble adhesives or binders which may be treated to render them water-resistant or water-insoluble include any of the well known starches (corn, rice, wheat, etc.), albumin, certain alginates, alges deribade, gelatins, sugars, molasses, etc.

Any of these or other well known agglutinates may be made water-resistant by suitable chemical treatment, particularly treatment with formaldehyde, bichromate, alum, etc. or dissolving the same in a solvent, such as cellulose in acetone.

It will be obvious to those skilled in the art that many modifications may be made within the scope of the present invention without departing from the spirit thereof, and the invention includes all such modifications.

What is claimed is:

1. A method of making a porcelain tooth structure, comprising preparing a paste of powder-form porcelain and an adhesive material, in an amount sufficient to form a cohesive mass of said porcelain, forming said paste into the general shape of a desired, finished porcelain tooth and drying said formed paste to produce an unbaked, dry, coherent tooth structure, said adhesive in at least part of said tooth structure being a water-soluble adhesive treated with an agent during the formation of the paste to render said adhesive water-resistant after drying, said agent entering into a physico-chemical reaction with said adhesive, and said adhesive being volatilizable below vitrification temperature and leaving no discoloring effect, and said porcelain being compatible with standard commercial porcelains so that when standard commercial porcelain is added to the structure and the entire structure is fired, a monolithic structure results.

2. A method in accordance with claim 1 wherein the agent to render the adhesive water-resistant is a solvent.

3. A method in accordance with claim 1 wherein the agent to render the adhesive water-resistant is a hardening agent.

4. A method in accordance with claim 1 wherein the agent to render the adhesive water-resistant enters into a chemical reaction with said adhesive.

5. A method in accordance with claim 1 wherein the agent to render the adhesive water-resistant has a physical effect on said adhesive.

* * * * *